(12) United States Patent
de La Poype et al.

(10) Patent No.: US 6,537,452 B1
(45) Date of Patent: Mar. 25, 2003

(54) CELL CENTRIFUGE PARTITION CHROMATOGRAPHY DEVICE

(75) Inventors: François de La Poype, Boulogne Billancourt (FR); Roland De La Poype, Paris (FR); Patrick Durand, Reze les Nantes (FR); Alain Foucault, Nantes (FR); Jack Legrand, Saint Nazaire (FR); Gérard Patissier, La Chapelle sur Erdre (FR); Jean-Michel Rosant, Nantes (FR)

(73) Assignees: Etudes et Application Industrielle de Brevets-SEAB, Villejuif (FR); Institut Francais de Recherche pour l'Exploitation de la Mer-Ifremer, Issy les Moulineaux (FR)

( * ) Notice: Subject to any disclaimer, the term of this patent is extended or adjusted under 35 U.S.C. 154(b) by 0 days.

(21) Appl. No.: 09/926,246
(22) PCT Filed: Mar. 31, 2000
(86) PCT No.: PCT/FR00/00830
§ 371 (c)(1),
(2), (4) Date: Sep. 28, 2001
(87) PCT Pub. No.: WO00/58722
PCT Pub. Date: Oct. 5, 2000

(30) Foreign Application Priority Data

Mar. 31, 1999 (FR) .............................................. 99 04050

(51) Int. Cl.⁷ .............................................. B01D 15/08
(52) U.S. Cl. ..................... 210/198.2; 210/657; 210/635
(58) Field of Search ................................. 210/635, 656, 210/657, 198.2

(56) References Cited

U.S. PATENT DOCUMENTS

| | | | | |
|---|---|---|---|---|
| 3,994,805 A | * | 11/1976 | Ito ............................... | 210/657 |
| 4,551,251 A | | 11/1985 | Kolobow et al. ........... | 210/635 |
| 4,632,762 A | * | 12/1986 | Ramsland ................... | 210/657 |
| 4,753,734 A | * | 6/1988 | Ito ............................... | 210/657 |
| 4,857,187 A | | 8/1989 | Ito .......................... | 210/198.2 |
| 4,968,428 A | | 11/1990 | Nunogaki ................... | 210/635 |

* cited by examiner

Primary Examiner—Ernest G. Therkorn
(74) Attorney, Agent, or Firm—Jacobson Holman PLLC

(57) ABSTRACT

A centrifuge partition chromatography device for separating a liquid into at least two phases, comprising at least one flat ring (3a) that can be rotationally driven around its axis, disposed in a substantially vertical position. Said ring (3a) comprises a plurality of cells (7) whose dimensions are greater in a first direction than the dimensions in a second direction which is substantially perpendicular to the first, disposed side by side and distributed along the periphery of said ring (3a) in addition to being connected to each other in a series by inlet and outlet ducts (15) terminating in the opposite respective ends of each cells (7) enabling the circulation of liquid. The invention is characterized in that said ducts (15) are disposed in such a way that the liquid supply jet penetrates the cells (7) in a direction that includes at least one radial component relative to the axis of rotation of said ring (3a).

8 Claims, 5 Drawing Sheets

CELL CENTRIFUGE PARTITION CHROMATOGRAPHY DEVICE

This is a 371 of PCT/FR00/00830 filed Mar. 31, 2000 and published in French.

The present invention relates to a centrifuge partition chromatography device comprising at least one flat ring adapted to be driven in rotation about its substantially vertically disposed axis and comprising cells connected by ducts.

Centrifuge partition chromatography is a method of separation of the compositions of a mixture between a mobile phase and a stationary phase for each of which the compositions have a different affinity.

The invention concerns more particularly a method of liquid-liquid separation of two non-miscible phases in contact with each other. One, called stationary phase, is maintained immobile inside the cells thanks to the centrifugal force to which it is subjected while the other, called mobile phase, percolates the stationary phase.

The efficiency of such a device, in order to obtain a good separation, depends on the flow of the mobile phase through the stationary phase. The more the jet entering in the cell is atomized, the better the efficiency of the device will be.

U.S. Pat. No. 4,968,428 discloses a counter-current chromatography device using stacked flat rings driven in rotation. These rings comprise a plurality of cells connected together in series by ducts engraved on said rings.

The orientation of the ducts of this device is such that the jet of liquid penetrates in each cell in a direction substantially tangential with respect to the rotation of the ring. This orientation causes flows of the mobile phase through the stationary phase which do not promote a good separation of the different elements. In effect, according to the visualizations made with the aid of an asynchronous camera and an ad hoc stroboscopic system, the jet tends to be applied relatively rapidly on the walls of the cells, which is detrimental to the performances of the system.

Based on this system of visualization, the present invention proposes a centrifuge partition chromatography device for separating a liquid into at least two phases, adapted to promote the dispersion of the mobile phase through the stationary phase and thus presenting a better efficiency.

To that end, according to the invention, the centrifuge partition chromatography device for separating a liquid into at least two phases, comprising at least one flat ring adapted to be driven in rotation about its axis, disposed substantially vertically, said ring comprising a plurality of cells whose dimension in a first direction is greater than the dimension in a second direction substantially perpendicular to the first, disposed side by side, distributed along the periphery of said ring and connected to each other in series by inlet and outlet ducts opening out at the respective opposite ends of said cells so as to allow the circulation of the liquid, is characterized in that said ducts are arranged so that the liquid supply jet penetrates in the cells in a direction including at least one radial component with respect to the axis of rotation of the ring.

The ducts are advantageously disposed so that the supply jet penetrates into the cells in a radial direction with respect to the axis of rotation of the ring.

According to a preferred form of embodiment, the direction of the largest dimension of each cell is radial.

According to another embodiment, the direction of the largest dimension of each cell is inclined with respect to the radial direction, to allow a better atomization of the jet deviated from this radial direction.

Each cell preferably presents, seen from above, a substantially quadrangular shape.

The inclination of the direction of the largest dimension is advantageously included between 10 and 50 degrees, preferably between 20 and 40 degrees, and preferentially of the order of 30 degrees.

According to a preferred form of embodiment, the dimension of the cells in the radial direction is greater than the dimension in the tangential direction.

According to another form of embodiment, the dimension of the cells in the tangential direction is greater than the dimension in the radial direction.

The cells as well as the ducts are preferably through ones.

The invention also relates to a centrifuge partition chromatography device for separating a liquid into at least two phases, comprising at least one flat ring adapted to be driven in rotation about its axis, disposed substantially vertically, said ring comprising a plurality of cells whose dimension in a first direction is greater than the dimension in a second direction substantially perpendicular to the first, disposed side by side, distributed over the periphery of said ring and connected to each other in series by inlet and outlet ducts disposed at opposite ends of said cells so as to allow the circulation of the liquid, and characterized in that the dimension of the cells in the tangential direction is greater than the dimension in the radial direction.

All the cells of the same ring are advantageously identical.

BRIEF DESCRIPTION OF THE DRAWINGS

The invention will be more readily understood on reading the following description relating to an illustrative but non-limiting example of embodiment, with reference to the accompanying drawings, in which.

DESCRIPTION OF THE PREFERRED EMBODIMENTS

Figure 1:
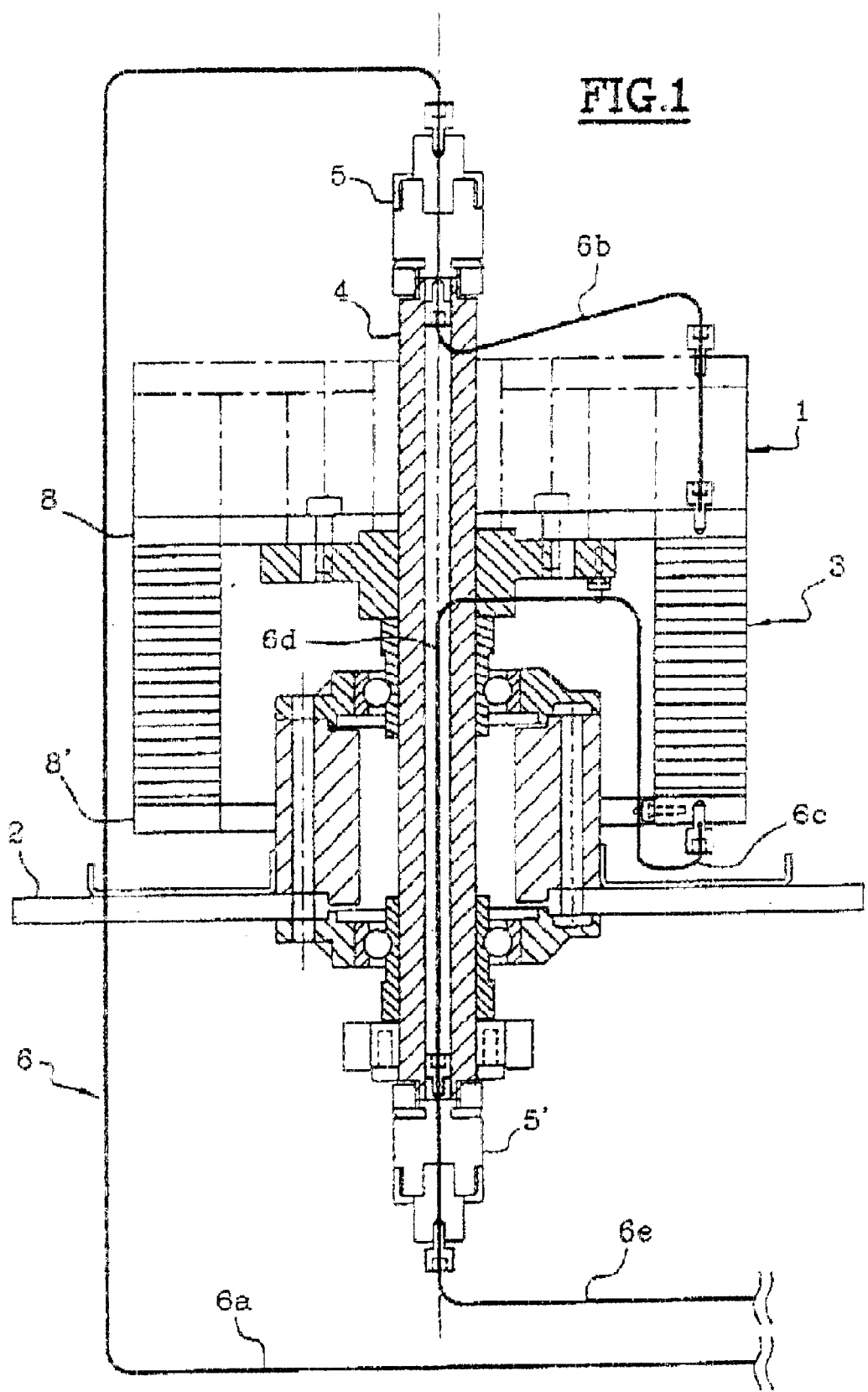
FIG. 1 is a general view in transverse section of the assembly of the device according to one embodiment of the invention.

With reference to FIG. 1, there is shown, in section along a vertical plane, a centrifuge partition chromatography device comprising a rotor 1 mounted on a table 2 and adapted to be driven in rotation about the vertically disposed axis A, via drive means which are known and not shown.

The rotor 1 is constituted by a plurality of stacked flat rings 3, of identical diameter and fast with a column 4 composed of a hollow tube disposed between two upper (5) and lower (5') rotating joints, of known architecture. The axis of rotation A corresponds to the axis of the stacked rings.

The column 4 is supplied with liquid composition through the joints 5 and 5' via a circuit of pipes 6 connected to supply and recovery means which are known and not shown.

The device being adapted to function in accordance with two modes, ascending and descending, each of the two rotating joints 5 and 5' may constitute either the inlet or the outlet of the system. The path of the liquid in the circuit 6 is materialized by the thick line in FIG. 1.

In the case of descending mode for example, a first branch 6a of the circuit 6 connects the supply means (such as a pump) to the upper rotating joint 5. After having traversed the rotating joint 5, a second branch 6b conducts the liquid up to the inlet of the rotor 1 and, after having traversed it, emerges therefrom in the lower part at the level of branch 6c. The branch 6d, located inside the column 4, conducts the liquid as far as the lower joint 5' which, after having traversed the joint, is recovered at the level of branch 6e, and conducted towards the recovery means.

In this way, the liquid under pressure enters at the level of the upper joint 5 to attain the stack of rings 3 by the top, passing through the column 4, then circulates inside the cells of the first ring, then those of the second, and so on, emerging at the lower level of the stack of rings 3 and passing through the column 4 as far as the lower rotating joint 5'. If the device functions in ascending mode, the path of the liquid is reversed.

Figure 2:
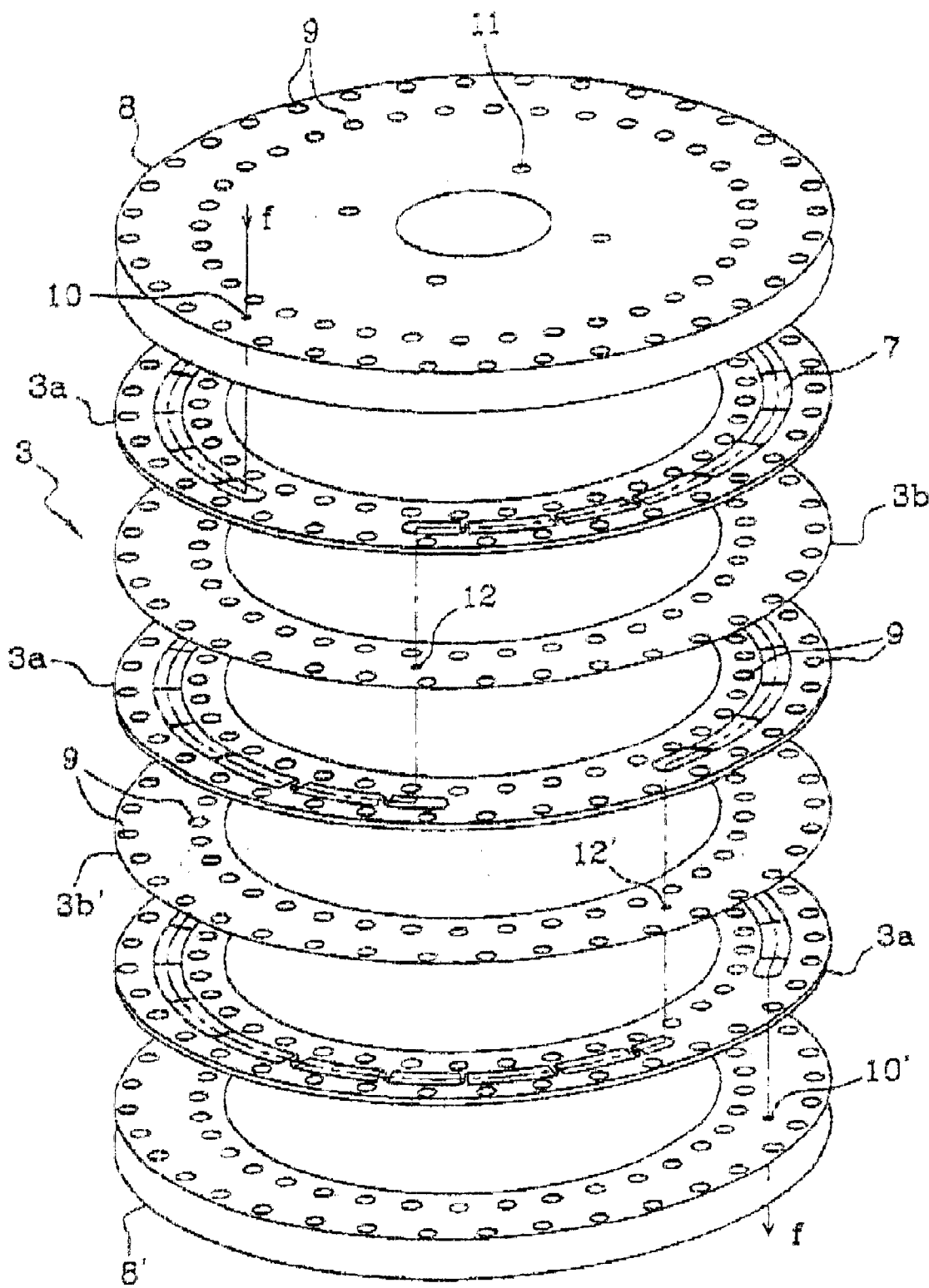
FIG. 2 is an exploded view in perspective of a stack of rings comprising cells of particular shape.

FIG. 2 shows in exploded perspective view a stack of rings 3 of the rotor according to a particular form of embodiment.

The stack is constituted, in the example shown, by three flat rings 3a comprising cells 7. Between two successive rings 3a there is inserted an annular joint 3b, 3b' in order to effect seal between the rings.

The assembly of the three rings 3a and of the annular joints 3b and 3b' is applied between two circular plates 8 and 8' having the same outer diameter as the rings. The upper plate 8 is substantially in the form of a disc while the lower plate 8' presents an annular shape.

Each of these seven elements, rings, annular joints and plates, comprise two concentric series of bores 9 at the level of their periphery in order to join them together with the aid of screws or pins (not shown). The plates further comprise holes 10 and 10' for passage of the liquid, disposed between the two series of bores 9. Furthermore, the upper plate 8 presents additional bores 11 disposed near the centre and enabling the assembly to be connected to the column 4.

The rings 3a present a series of identical cells 7 disposed side by side and distributed over virtually the whole periphery of the rings 3a between the two series of bores. The cells 7, described in greater detail in relation with FIGS. 3 to 8, are made either by recessing of matter on the ring (in that case they are so-called "through" ones), or are simply engraved.

The annular joints 3b, 3b' may be made of supple material such as Teflon (registered Trademark) for example. They each comprise, like plates 8 and 8', an additional hole 12, 12' adapted to allow the liquid to pass upon its passage between two consecutive rings 3a.

The path of the liquid through the stack of rings, in the case of descending mode, is materialized by the discontinuous line referenced f.

The rotating assembly is supplied with liquid at the level of the hole 10 in the upper plate 8 which the liquid traverses in order to attain the first ring 3a. It penetrates in the first cell 7 then passes from cells to cells through ducts described hereinbelow connecting one cell to the following, as far as the last cell of the ring. There, the liquid traverses the annular joint 3b via the hole 12 and passes through cells 7 of the second ring 3a and so on until the lower plate 8' is attained. After having traversed the hole 10' provided in the latter, the liquid is then conducted towards the hollow column 4 (branches 6c and 6d of the circuit 6 in FIG. 1).

In the case of ascending mode, the path of the liquid is the reverse of the preceding one.

Figure 3:
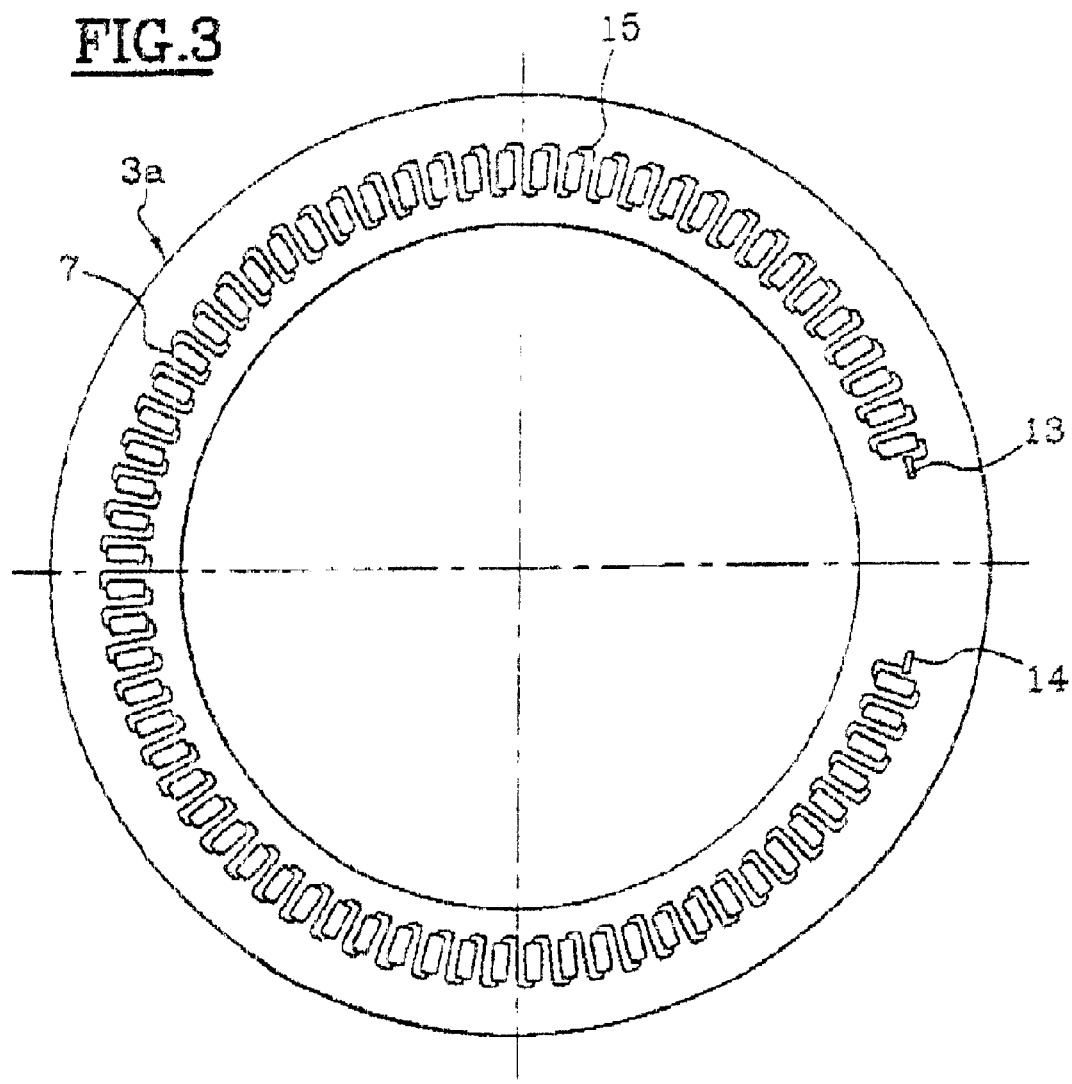
FIG. 3 is a view from above of a ring comprising a first form of embodiment of the cells.
Figure 4:
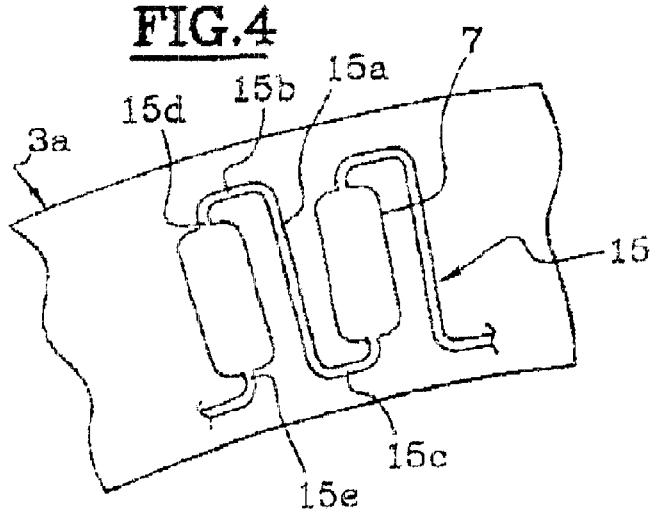
FIG. 4 is a detail in plan view of the cells of FIG. 3.

FIGS. 3 and 4 show, in view from above, a first form of embodiment of the cells 7 of a ring 3a according to the invention.

For all of FIGS. 3 to 8, the two series of bores 9 for fixation have not been shown in order to render the drawings clearer. For the same reason, the scale of distances between the cells 7 and the edges of the ring has not been respected.

The ring 3a comprises a plurality of cells 7 distributed over virtually the whole of its periphery between an inlet cell 13 and an outlet cell 14. It should be noted that, depending on the direction of passage of the fluid, the inlet cell becomes the outlet cell.

Each cell 7 is connected to the adjacent cell via a narrow duct 15 opening out at the respective ends of each cell and substantially in the middle in the tangential direction. As indicated hereinabove, the cells 7 as well as the ducts 15, of generally cylindrical shape, may be either engraved or pierced through the ring and are in that case called "through" ones.

For all the Figures, "radial" qualifies any direction parallel to a radius of a ring 3a and "tangential" any direction perpendicular to a radius of a ring.

The cells 7 are all identical and of substantially quadrangular shape and the direction of the largest dimension is radial. By way of indication, possible dimensions for the cells are:

Width (tangential dimension): 4 mm
Length (radial dimension): 9.8 mm

Connection of each duct 15 to two successive cells is effected at the level of the radial ends of the cells 7. In this way, the jet of liquid penetrates in the cell in a direction at least substantially radial and preferably radial, and this both in ascending and descending mode.

To that end, with reference to FIG. 4, each duct 15 connecting two consecutive cells comprises a first substantially radial section 15a included between two substantially tangential sections 15b and 15c. Each of the latter is connected to the corresponding cell via a second radial section 15d, 15e itself connected to the cell so that the liquid opens out in the cell in a radial direction.

Thanks to this arrangement of the ducts 15 with respect to the cells 7, the mobile phase is injected in the cells substantially radially, which promotes its atomization and thus increases the efficiency of the device.

The diameters of the ducts are included between 0.5 and 1 mm, preferably of the order of 0.7 mm.

Figure 5:
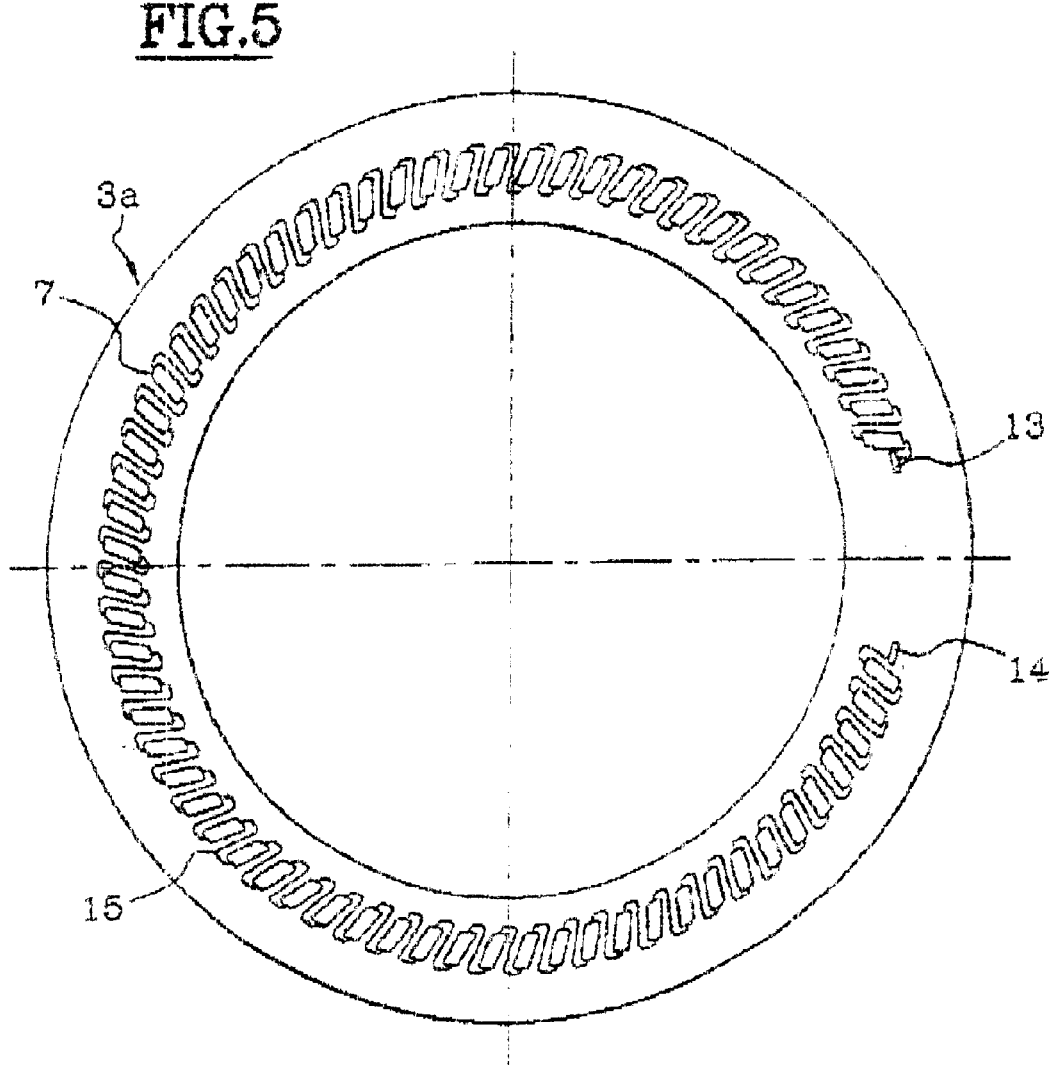
FIG. 5 is a view from above of a ring comprising a second form of embodiment of the cells.
Figure 6:
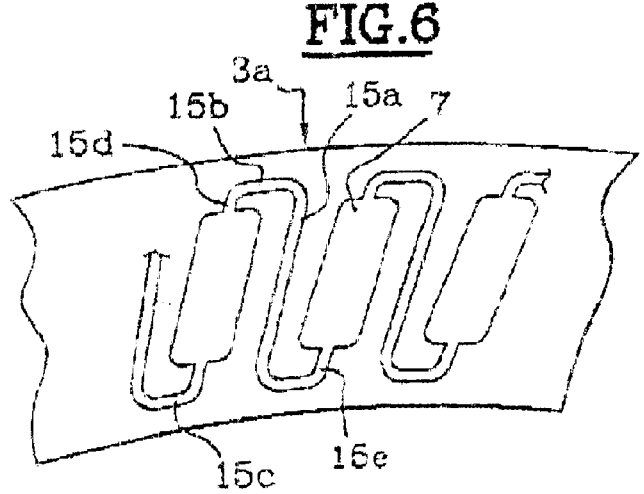
FIG. 6 is a detail in plan view of the cells of FIG. 5.

FIGS. 5 and 6 describe a second form of embodiment of the cells 7 and the ducts 15.

The general geometry is quite similar to that of the cells of FIGS. 3 and 4 but, in this case, the direction of the largest dimension of the cells is no longer radial but inclined with respect to a radius of the ring 3a.

In effect, the principal direction of the cells 7 presents an inclination of between 10 and 50 degrees, preferably between 20 and 40 degrees, and advantageously of the order of 30 degrees.

The section of duct 15a which was parallel to the direction of the largest dimension of the cells in FIGS. 3 and 4, remains parallel to this direction and therefore presents the same inclination as the cells 7.

However, the sections of ducts 15d and 15e, opening out in the cells, are radial in order to continue to benefit from a radial injection of the mobile phase. The point of connection of these sections of duct to the cells is slightly offset with respect to the axis of symmetry of the cells contrarily to the form of embodiment of FIGS. 3 and 4.

Figure 7:
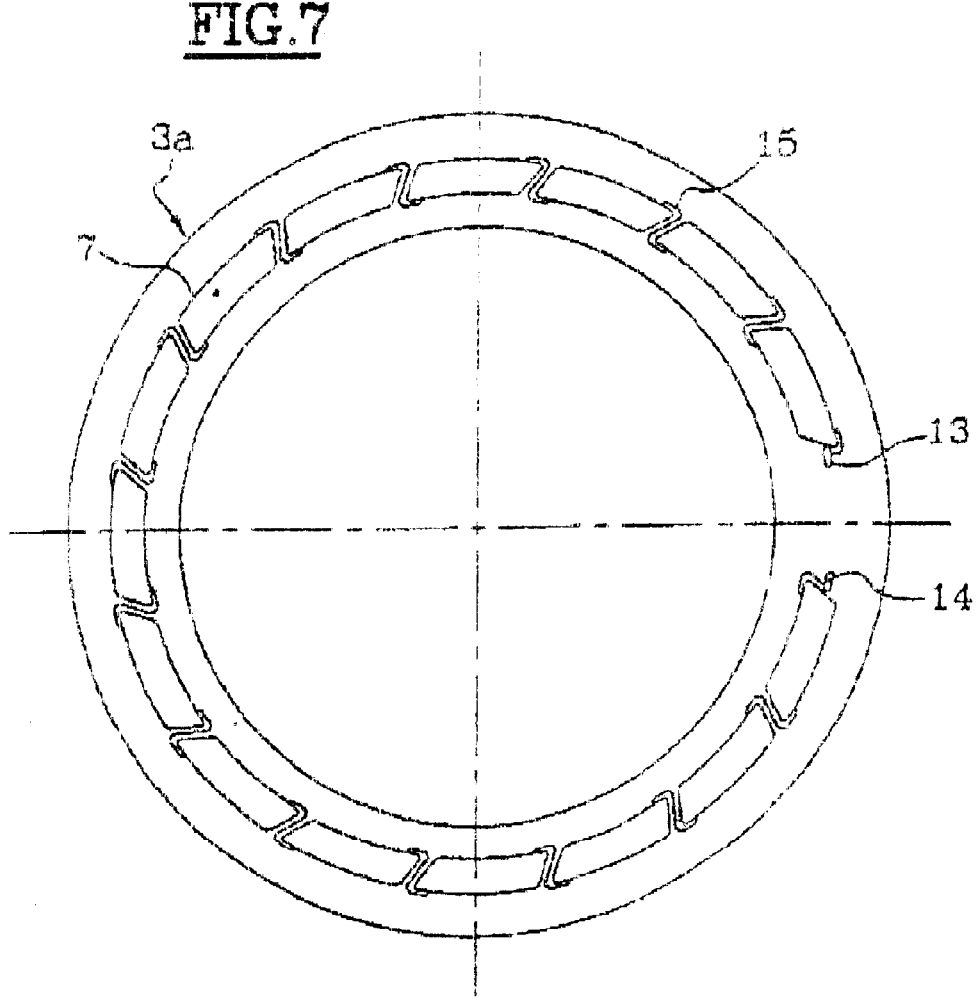
FIG. 7 is a view from above of a ring comprising a third form of embodiment of the cells.

FIG. 7 describes a third shape of cells, still distributed over virtually the whole periphery of a ring 3a.

In this case, the cells present the same inclination as in FIGS. 5 and 6, but the tangential dimension of each cell is greater than the radial dimension. For example, the radial dimension might be about 10 mm, while the tangential dimension would be 35 mm for an inclination of about 30 degrees.

Ducts 15, in particular their connection 15d and 15e to two adjacent cells 7, are identical to those of FIG. 6, always allowing a radial injection of the mobile phase into the stationary phase.

This type of geometry of cells, wider than high, is particularly suitable for the biphase aqueous systems used for example in the purification of biopolymers (DNA, nucleotides, proteins).

Figure 8:
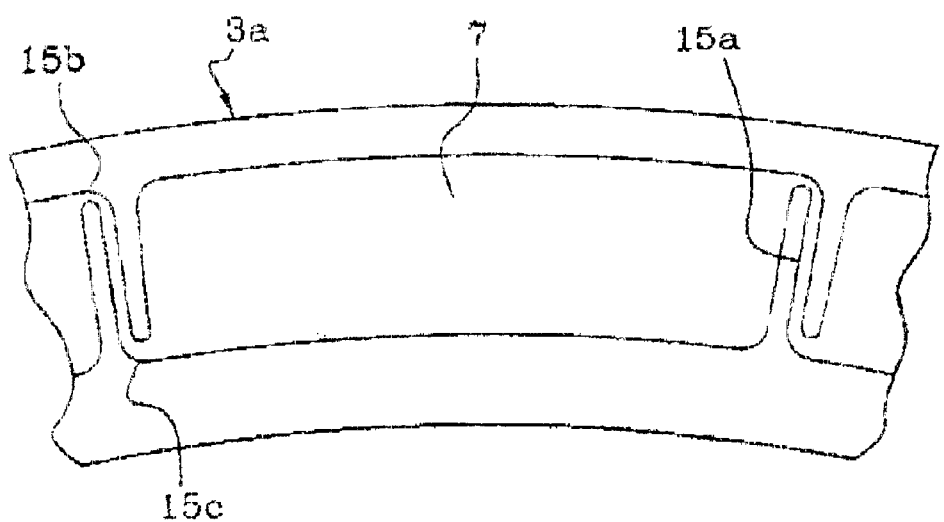
FIG. 8 is a detail in plan view of another form of embodiment of the cells of FIG. 3.

FIG. 8 shows a fourth form of embodiment of the cells 7 and of the ducts 15.

In this form of embodiment, the cells are not inclined with respect to a radius of the ring 3a, and (as for those of FIG. 7), their tangential dimension is larger than their radial dimension.

The ducts 15 connecting two consecutive cells comprise a substantially radial section 15a directly connected to each cell via a substantially tangential section 15b, 15c, so that the supply of mobile phase to said cells is tangential.

In this way, thanks to the particular geometry of its cells, the device according to the invention is capable of promoting the dispersion of the mobile phase through the stationary phase, thus procuring a better efficiency.

What is claimed is:

1. Centrifuge partition chromatography device for separating a liquid into at least two phases, comprising at least one flat ring 3a adapted to be driven in rotation about its axis, disposed substantially vertically, said ring 3a comprising a plurality of cells 7 whose dimension in a first direction is greater than the dimension in a second direction substantially perpendicular to the first, disposed side by side, distributed along the periphery of said ring 3a and connected to each other in series by inlet and outlet ducts 15 opening out at the respective opposite ends of said cells 7 so as to allow the circulation of the liquid, said ducts 15 being arranged so that the liquid supply jet penetrates in the cells 7 in a direction including at least one radial component with respect to the axis of rotation of the ring 3a, characterized in that the direction of the largest dimension of each cell 7 is inclined with respect to the radial direction.

2. Device according to claim 1, characterized in that the inclination of the direction of the largest dimension is included between 10 and 50 degrees.

3. Device according to claim 1, characterized in that each cell 7 presents, seen from above, a substantially quadrangular shape.

4. Device according to claim 1, characterized in that the cells 7 are through ones.

5. Device according to claim 1, characterized in that the ducts 15 are through ones.

6. Device according to claim 1, characterized in that all the cells 7 of the same ring 3a are identical.

7. Device according to claim 1, characterized in that the inclination of the direction of the largest dimension is included between 20 and 40 degrees.

8. Device according to claim 1, characterized in that the inclination of the direction of the largest dimension is about 30 degrees.

* * * * *